United States Patent [19]

Horiuchi et al.

[11] 4,358,953
[45] Nov. 16, 1982

[54] METHOD OF MONITORING THE WEAR OF REFRACTORY WALLS OF A BLAST FURNACE AND TEMPERATURE PROBE USED FOR THE METHOD

[75] Inventors: Takefumi Horiuchi, Kobe; Yoshio Kawate, Toyonaka; Masami Konishi, Akashi; Nobuyuki Nagai, Kobe, all of Japan

[73] Assignee: Kobe Steel, Ltd., Kobe, Japan

[21] Appl. No.: 183,452

[22] Filed: Sep. 2, 1980

[51] Int. Cl.³ ..................... G01N 17/00; G01K 1/02
[52] U.S. Cl. ........................................ 374/7; 73/86; 374/137
[58] Field of Search ................. 73/86, 340, 341, 342, 73/343 B

[56] References Cited

U.S. PATENT DOCUMENTS

| | | | |
|---|---|---|---|
| 3,018,663 | 1/1962 | Dunlop | 73/341 |
| 3,307,401 | 3/1967 | Bachman | 73/86 |
| 3,512,413 | 5/1970 | Krusenstierna et al. | 73/341 |
| 3,526,123 | 9/1970 | Putman et al. | 73/341 |
| 3,532,797 | 10/1970 | Lunig | 73/86 |
| 3,532,797 | 10/1970 | Lunig | 73/86 |
| 3,955,419 | 5/1976 | Barton et al. | 73/340 |
| 4,103,539 | 8/1978 | Worley | 73/86 |
| 4,242,907 | 1/1981 | Kazmierowicz | 73/341 |

*Primary Examiner*—Donald O. Woodiel
*Attorney, Agent, or Firm*—Oblon, Fisher, Spivak, McClelland & Maier

[57] ABSTRACT

A method of monitoring the wear of refractor walls of a blast furnace wherein temperature is sensed at different points across the thickness of the furnace walls and various electric representations of the internal phenomena of the blast furnace are derived as trigger signals. Analysis is carried out as to the correlation between the trigger signals and variations in the temperatures at the furnace walls in terms of the time delay, thus predicting the present status of the wear of the furnace walls. A temperature probe assembly is also disclosed which is useful in sensing the temperature distribution of the refractory walls. The temperature probe assembly includes a plurality of parallel sheath type thermocouples or thermometers.

8 Claims, 6 Drawing Figures

DISTANCE FROM INSIDE SURFACE OF REFRACTORY WALL
($P_x, P_y, P_z$: ZERO POINTS AT RESPECTIVE TIME DELAYS)

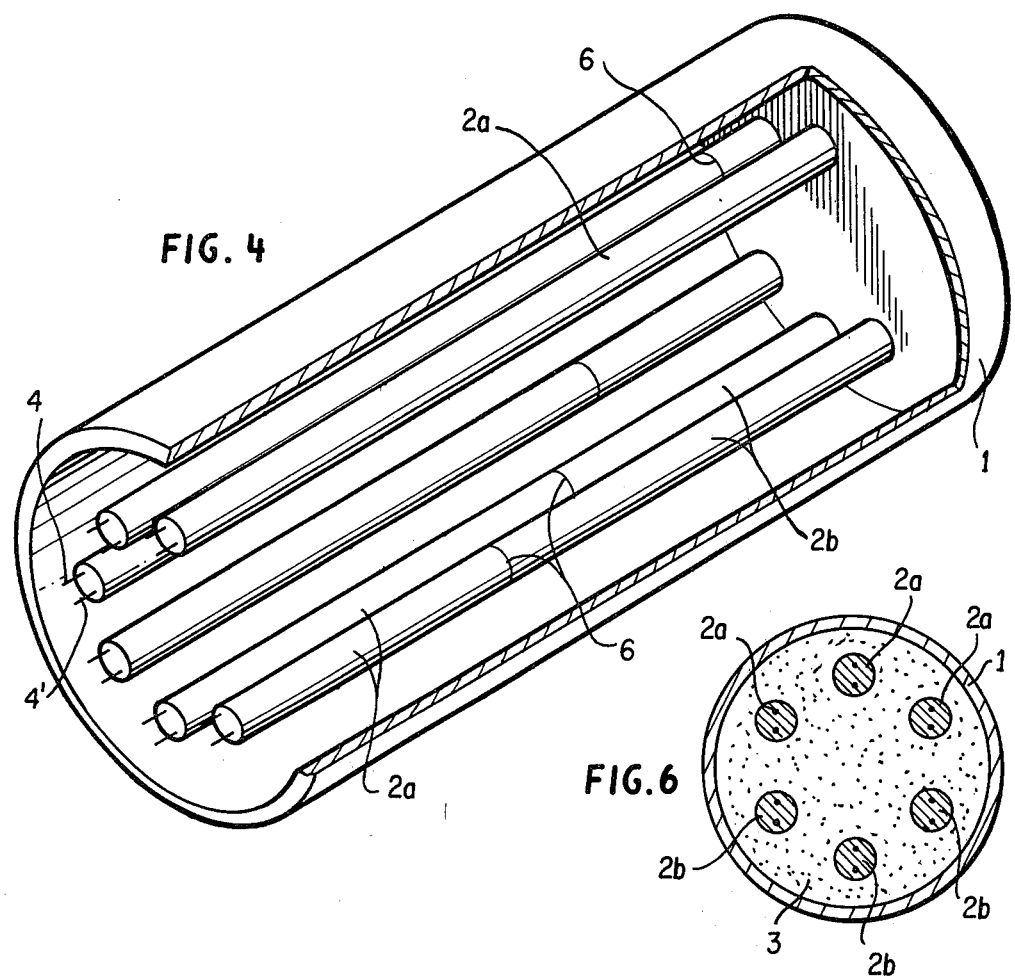
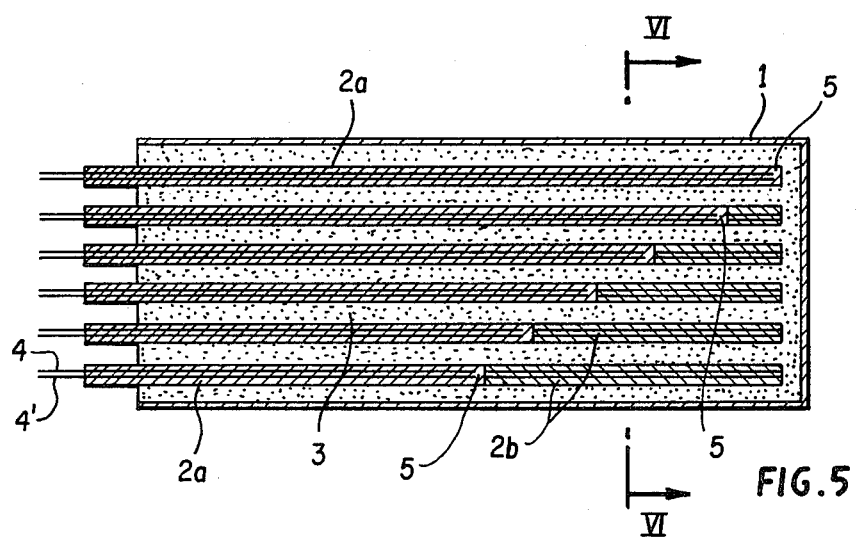

METHOD OF MONITORING THE WEAR OF REFRACTORY WALLS OF A BLAST FURNACE AND TEMPERATURE PROBE USED FOR THE METHOD

BACKGROUND OF THE INVENTION

1. Field of the Invention

This invention relates to a method of monitoring accurately the wear of refractory lining walls of a blast furnace due to high temperatures and other factors and a temperature probe assembly used for the method.

2. Description of the Prior Art

The blast furnace is a high temperature metallurgical reactor for solid reducing agents such as iron oxide materials including iron ore and coke, which includes refractory walls and its surrounding iron shell. Drilling the iron shell and filling a refractory repairing material are however necessary every time the refractory walls are eroded or exfoliated in various points since the interior of the blast furnace is kept at a high temperature and constantly subject to falling impact and friction by the iron ore or coke. In the past, it was as a matter-of-fact impossible to monitor accurately the wear of the refractory walls and even the primitive procedure using the reddening of the iron shell as an indicator was sometimes followed. Studies were universely made in an attempt to monitor theoretically the instantaneous thickness of the refractory walls and one approach of those studies will be presented below by way of example.

FIG. 1 is a diagram for explanation of the prior art analysis approach, wherein a refractory brickwork with a heat conductivity of $k_1$ is designated $1a$, a refractory brickwork with a heat conductivity of $k_2$ is designated $1b$, and an iron shell is designated 2. The point A shows the inside surface of the brickwork $1a$ with a temperature of $T_0$ and the point B shows the boundary between the two brickworks $1a$ and $1b$. The point C designates a specific point in the refractory brickwork $1b$ having a temperature of $T_2$ and the point D designates the boundary between the brickwork $1b$ and the iron shell 2 having a temperature of $T_3$. Reference symbols $l_1$, $l_2$ and $l_3$ designate the A-to-B distance, the B-to-C distance and the C-to-D distance, respectively. It is obvious from FIG. 1 that the brickworks $1a$ and $1b$ are made of different refractory linings, conventionally chamotte brick for the former and carbon brick for the latter. If the heat conductivities $k_1$ and $k_2$ of the brickworks $1a$ and $1b$ are fixed and the one-dimensional heat flow across the thickness of the refractory brickworks $1a$ and $1b$ is constant, then the following simultaneous equations will exist:

$$k_1 \frac{T_0 - T_1}{l_1} = k_2 \frac{T_1 - T_2}{l_2}$$

$$k_2 \frac{T_1 - T_2}{l_2} = k_2 \frac{T_2 - T_3}{l_3}$$

Since $k_1$ and $k_2$ are known and $T_0$ can be regarded as the melting point (say, 1150° C.) of iron, the remaining unknown values are $l_1$, $l_2$, $l_3$, $T_1$, $T_2$ and $T_3$. Where a temperature probe is inserted from outside the iron shell 2 so as to sense the temperature $T_2$ at the point A with the given depth and the temperature $T_3$ at the point D on the external surface of the refractory brickwork $1b$, $l_3$, $T_2$ and $T_3$ as well as $l_2$ may be specified because of $l_2 + l_3$ being a value set in the stage of designing the refractory brickworks. The only unknown values are $l_1$ and $l_2$ which may then be evaluated from the above simultaneous equations. Accordingly, it is able to realize the degree of wear of the refractory brickwork $1a$ and the temperature at the boundary between the refractory brickworks $1a$ and $1b$ for prediction of wear.

While being available as a device for estimating the remaining thickness of the refractory brickworks, the above mentioned method has several disadvantages as follows: In the foregoing the heat conductivities $k_1$ and $k_2$ of the refractory brickworks are considered as constant. These brickworks are necessarily subject to high temperature conditions for a great deal of time and especially the inside brickwork $1a$ would have been considerably deteriorated with an attendant variation of its heat conductivity ($k_1$). These serious phenomena were not taken into consideration in the past. Otherwise, $T_0$ is considered as being stationary at 1150° C. in the above discussion. However, should foreign matters originating from iron ore or coke be attached onto the inner surface of the refractory brickwork $1a$, $T_0$ would have fallen below 1150° C. This is another serious problem. Provided that no hot metal has yet developed in the proximity of the furnace body, $T_0$ may not reach 1150° C. Contrarily, $T_0$ may go far beyond 1150° C. due to a back blast. Any mechanism for tracing such variations in $T_0$ was not available in the prior art. Although it seems possible to increase the number of the temperature-measuring points across the thickness of the walls in order to enhance accuracy, this approach has the outstanding problem of how to determine or estimate the temperature $T_0$ and thus great difficulty in monitoring accurately the wear of the refractory brickworks as long as it falls within the category of the prior art.

SUMMARY OF THE INVENTION

With the above discussed disadvantages and shortcomings in mind, it is an object of the present invention to provide a method which makes possible monitoring accurately the wear of refractory walls without estimating unreasonably unknown values as experienced in the prior art.

It is another object of the present invention to provide a temperature sensing probe assembly which senses temperature distribution in a specific direction throughout furnace walls for monitoring the wear of the furnace walls due to aging.

In one noted aspect of the present invention, a method of monitoring wear includes sensing not only temperatures at furnace walls but also various electric representations of the internal phenomena of a blast furnace as trigger signals and analizing the correlation between the trigger signals and variations in the temperatures at the furnace walls in terms of time delay, thus estimating the present status of the furnace walls from the time delay at respective points.

Another significant feature of the present invention lies in an improved temperature probe assembly wherein a plurality of sheath type thermocouples or sheath type resistance thermometers are juxtaposed within a sheath enclosure and the tips of respective temperature sensing areas at different points across the length of the probe assembly are connected to thermocouples or the like made of the same material as the first-named thermocouples or the like, such sheath enclosure being filled with an insulating filler with the thermocouples or the like kept out of contact with each other. Such an arrangement reduces the amount of residual gas in the sheath enclosure to a minimum and curbs heat transmission across the length of the enclosure to enhance a high degree of accuracy. In addition, the cross sections of the respective temperature sensing areas assume the same configuration across the length of the probe assembly, thereby unifying conditions of measuring temperatures.

BRIEF DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts through the several views and wherein:

FIG. 4 is a perspective view partially in cross section showing a temperature probe according to the present invention;

FIG. 5 is a cross sectional side view of the temperature probe shown in FIG. 4; and FIG. 6 is an exploded cross sectional view of the temperature probe.

DETAILED DESCRIPTION OF THE PREFERRED EMBODIMENT

Figure 1:
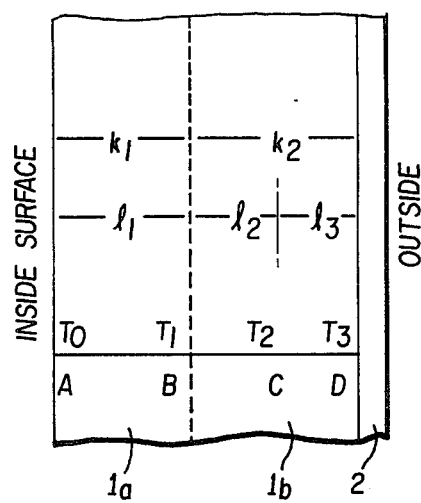
FIG. 1 is a representation illustrating the concept of the prior art.

Into a blast furnace are introduced iron ore, coke, etc. from top and hot air from bottom so that reducing reactions take place when the both meet within the furnace. Furnace operating conditions, however, vary from time to time according to the composition of starting materials and other factors as the reactions go on advancing within the furnace. Manifold measuring tools are installed on the top or a nozzle port of the furnace to monitor the efficiency of gas utilization, gas temperature, etc. The outputs of those measuring tools reflect the results of complicated phenomena occurring within the furnace. Apart from the fact that these internal phenomena of the blast furnace are well represented by the outputs appearing on the top of the furnace, they are generally believed to affect largely refractory walls of the furnace. Temperature is considered as the most significant factor in those phenomena. For instance, as the reducing reactions advances vigorously within the furnace, the efficiency of gas utilization and thus the internal temperature of the furnace increase with an increased amount of heat transmitted to the refractory walls.

Even when gas on the top of the furnace forms a central flow, the reactions are active and the amount of heat conveyed to the refractory walls is great. Since transfer of heat to the refractory walls is equivalent to a heat conduction in its narrowest sense, it has been confirmed by experiments that variations in the internal temperature of the refractory walls appear earlier on the central side of the furnace than on the iron shell side as represented by the outputs on the top of the furnace. The inventors call signals originated from the internal phenomena of the furnace which give rise to variations in temperature at the refractory walls, "trigger signals" and such a differential time "delay time" hereinafter. When there is a variation in temperature at the expiration of a considerable amount of time from the development of the trigger signals, the location of such variation in temperature is assumed to be still protected by its inner thick refractory wall portion.

For such analysis measurements of temperature should be conducted at as many points on the refractory walls as possible. Although a temperature distribution probes as discussed below is most desirable for this purpose, any other type of temperature probes including conventional multi-point temperature probes and future temperature probes are available for the purpose of the present invention. What kind of the temperature probes is used is immaterial for the present invention. While the trigger signals reflecting the above-mentioned efficiency of gas utilization of gas temperature distribution are most favorable, the trigger signals may be characteristic of other actual values such as the rate of the top gas flow and gas pressure alone or in combination. In any case, it is essential to obtain electrical representations of the internal phenomena of the furnace accurately and promptly by use of any measuring tool.

Figure 2:
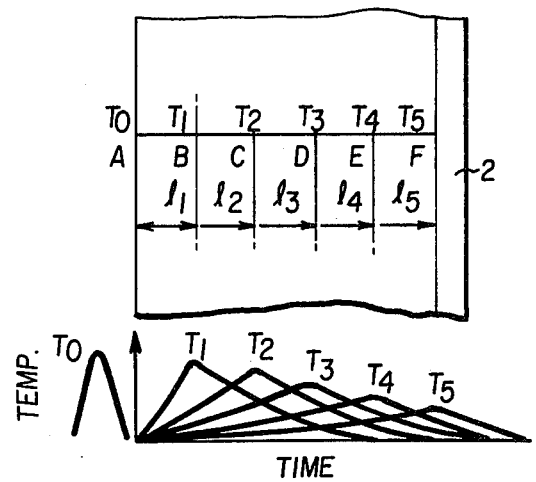
FIG. 2 is a representation illustrating the concept of the present invention.

FIG. 2 is similar to FIG. 1 but is a diagram for explanation of the present invention, wherein A, B, C and D designate temperature measuring points and $T_1$, $T_2$, $T_3$, . . . designate temperatures as sensed at the respective measuring points. The method of the present invention analyzes the results of measurements in the following manner rather than using the absolute values of the temperatures as sensed at the respective measuring points. A graph at a lower portion of FIG. 2 is plotted with temperature as as ordinate and time as as abscissa. The curve $T_1$ represents variations in the temperature as sensed at the point B with the progress of time, the curve $T_2$ indicates variations in the temperature at the point C and so forth. These variations in temperature correspond to those (sharp increase) at the point $T_0$ as depicted on the left hand of the ordinate, with the maximum temperature at the point $T_0$ being detected as the trigger signals. If the constantly varying temperatures at the respective measuring points are traced in graphs with the zero point of the abscissa being crossed by at the time when the trigger signals are detected, then each of the peak temperatures at the respective measuring points appears more slowly on the iron shell side 2 than on the refractory wall side. Such a delay is called a "time delay".

Figure 3:
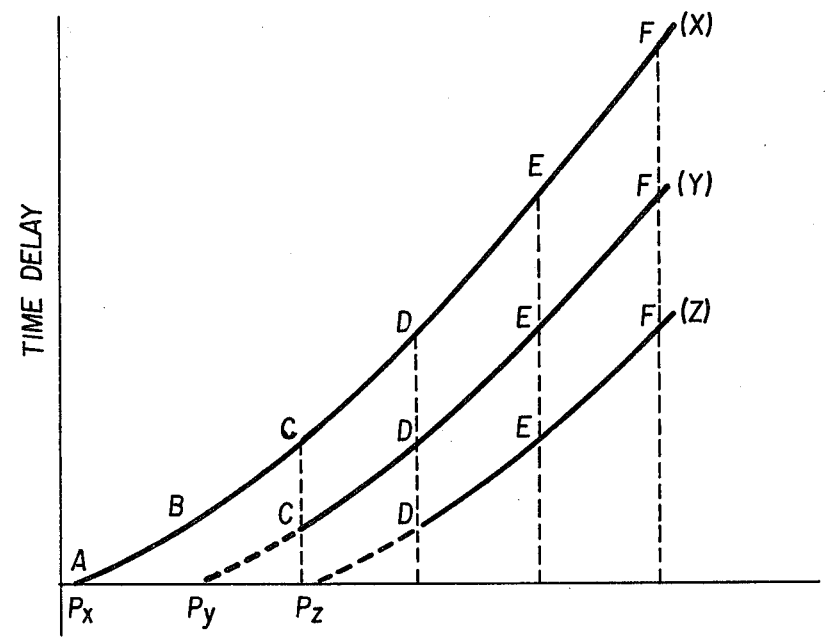
FIG. 3 is a graph showing the relationship between the time delay and the distance from an inner refractory wall.

The distances $l_2$, $l_3$, $l_4$ and $l_5$ between the two adjacent measuring points are known as determined by embedding the temperature probes and $l_1$ is also a value fixed at the beginning of operation of the blast furnace. Since there is the possibility that the temperature varying at $T_0$ is derived directly from the probes at the initial stage where no refractory walls are degraded, zero adjustment is possible for the following analytical method as long as the differential time between the occurance of variations in temperature and the development of the trigger signals is previously known. The curve (X) in FIG. 3 depicts the results of the zero adjustment, indicating the time delays actually measured at the respective points. It will be noted that the crossing $P_x$ of the curve (X) with the abscissa rests on the zero point. The point A is located on the closest inside surface of the refractory walls and the point F is farthermost from the inside surface. The entire thickness of the refractory walls can be defined theroetically as follows:

$(l_1)+(l_2)+(l_3)+(l_4)+(l_5)$

Assume now that the wear of the refractory walls advances from the point A to the point B. It becomes impossible to monitor temperature at the point B as well as the point A with the remaining points C–F still available for temperature measurements. The curve (Y) is plotted with the actual time delays in the same manner as with the curve (X). The phantom line leading from the point C is shown to obtain a possible intersection $P_y$ with the abscissa. The point $P_y$ corresponds to the point where the time delay is zero and helps predict the location of the closest inside surface of the refractory walls even though the points A and B have not been available for measurements any more. With a further advance in the wear of the refractory walls, difficulty is encountered in measuring temperature at the point C rather than the remaining points D, E and F. As a result, the curve moves to the right downwardly as denoted by (Z) since the distances between the points D–F and the closest inside surface of the refractory walls as represented by the time delays at the respective points become shorter in accordance with the advance in the wear. It is also possible to predict the zero point (namely, the location of the closest inside surface of the refractory walls) by interposing the phantom line. The above discussed analysis is carried out to monitor the wear by use of the analog time delays, whereas such time delays can be evaluated digitally from the following equation which indicates the correlation between the trigger signals $S_1$ and $T_1$:

$$\phi_{ST_1}(n) = \frac{1}{M-n} \sum_{i=1}^{M-n} S(i)T_1(i+n)$$

$$(n = 0 \sim M)$$

wherein
S: the trigger signals
T: the temperature sensed by the probes
$T_1$: the temperature detected at the point B of FIG. 2
i,n: the lapsed time
$\Delta\tau$: the time delays
$\phi$: coefficiency of the correlation between the trigger signals and the time delays The stationary point calculation can be executed with regard to $\phi_{ST_1}(n)$, depending on the results of evaluation. A typical example of the stationary point calculation is now discussed. If a specific stationary point where $n = n_0$, then $$\text{Min.}|\phi_{ST_1}(n) - \phi_{ST_1}(n-1)| = |\phi_{ST_1}(n_0) - \phi_{ST_1}(n_0-1)|$$

Consequently, $$\Delta\tau_1 = \Delta t \cdot n_0$$

wherein $\Delta t$ is the sampling interval. Accordingly, the time delay $\Delta\tau_1$ between $T_0$ and $T_1$ can be evaluated as follows:

$$\Delta\tau_1 - \Delta\tau_0$$

wherein $\Delta\tau_0$ is the amount of the zero adjustment.

Similarly, it is possible to evaluate $\Delta\tau_2$, $\Delta\tau_3$ and so on and specify the points B–F of FIG. 3. Then, the location of the wear of the refractory walls can be found while tracing the curves traversing the respective measuring points and calculating the possible intersections where the abscissa of the curves cross the zero point.

The monitoring method according to the present invention is advantageous over the prior art method as follows:

(1) The wear of the refractory walls is accurately monitored without the need to limit $T_0$ to 1150° C. or select $T_0$ as an input as experienced in the prior art.

(2) Since analysis is accomplished without treating $K_1, K_2, \ldots$ as fixed values, it is possible to predict the degree of wear whether the refractory walls have been degraded.

(3) Monitoring by the temperature probe assembly relies upon the absolute values of temperature per se but the correlation between the trigger signals and the time delays is without any influence of reduced accuracy.

FIG. 4 is a perspective view partly in cross section of the temperature probe assembly useful with the monitoring method as previously discussed with an insulator filler omitted. FIG. 5 shows an example of the temperature probe assembly wherein only six sheath type thermocouples are shown as being accommodated and FIG. 6 is an exploded cross sectional view taken along the line VI—VI of FIG. 5.

A sheath enclosure 1 serves as a protector for the entire temperature probe assembly. It is obvious to those skilled in the art that sheath type resistance thermometers may replace the sheath type thermocouples $2_a$ shown in those drawings. A pair of metallic wires 4 and 4' having thermoelectric effects are inserted into each of the thermocouples $2_a$, both of which form a measuring contact 5 (temperature sensing area) at its tip portions. These temperature sensing areas are located at different positions across the thickness of the probe assembly. Although the temperature sensing areas are shown as being equally spaced, they may be located at different intervals or even at random. Each of the temperature sensing areas 5 is provided at its tip portion with a sheath type thermocouple $2_b$ which serves as a dummy element and includes exactly the same material as the sheath type thermocouple $2_a$. Well known connectors 6 are used but it is not mandatory that the metallic wires 4 and 4' be connected to each other. In another example illustrated in FIG. 3, the uppermost thermocouple $2_a$ is not connected to the dummy thermocouple in order that its foremost end may be embedded to its deepest position. The present invention is intended to encompass not only such an arrangement but also another modification as discussed below. As seen from FIG. 6, the sheath enclosure 1 extends to the right such that the dummy thermocouple may be connected to the uppermost thermocouple $2_a$ and the counterparts associated with the respective remaining lower thermocouples $2_a$ extend correspondingly.

A filler 3 is made of an appropriate insulating material and is preferably heatproof material such as magnesia when the probe assembly is installed within the blast furnace discussed above. The effect of the filler is to enhance the durability of the sheath type thermocouples $2_a$ and suppress heat transmission along the length of the probe assembly with resulting in a high degree of accuracy in measuring temperature distribution along the length of the probe assembly. It is recommended that the sheath enclosure be thinner and made of a material with a lower heat conductivity in order to attain a further reduction in heat transmission along the length of the probe assembly. If the probe assembly demands resistance to corrosion, stainless steel, Inconel, etc. are desirable.

One way to increase the density of the filler material and minimize the amount of the residual air is by reducing the diameter of the sheath enclosure. This provides integrality of the probe structure and keeps the relative positions between the sheath type thermocouples $2_a$ constantly fixed.

As stated above, in the temperature sensing probe assembly according to the present invention, the respective temperature sensing areas assume the same cross section to equal the measuring conditions and minimizes heat transmission across the length of the probe assembly, thus ensuring highly reliable measurements of temperature distribution throughout the probe assembly. When the probe assembly is used as the sensor for monitoring the wear of the refractory walls as fully discussed above, it provides continued observations of fluctuations in temperature distribution and prediction of the time when the refractory walls become worn out. In addition, the temperature sensing probe assembly is free of any decrease in accuracy due to convection of gas or any fluid leaking from its surroundings via the damaged protector with a minimum amount of the residual air in the probe assembly.

Other significant advantages offered by the present temperature probe assembly are highly reliable measurement results and a high degree of security. It is evident that the probe assembly according to the present invention is equally applicable to measure the temperature distribution of liquid or gas in addition to that of solid material such as the refractory walls of the furnace.

Whereas the present invention has been described with respect to specific embodiments thereof, it will be understood that various changes and modifications will be suggested to one skilled in the art, and it is intended to encompass such changes and modifications as fall within the scope of the attended claims.

What is claimed as new and desired to be secured by letters patent of the United States is:

1. A method of monitoring the wear of refractory walls of a blast furnace wherein the furnace walls have temperature probes embedded therein, comprising the steps of:
    developing electric representations of the internal phenomena of the blast furnace as trigger signals;
    measuring temperatures at different points across the thickness of the furnace walls by the temperature probes embedded in the refractor walls; and
    analyzing the relation of the time delay for each trigger signal and temperature probe output signals correlated with the radical distance between the temperature measuring points and the center of the furnace so as to predict location of wear of the refractory walls.

2. A method according to claim 1 wherein said time delay is defined by the time when the temperature sensed at respective different points shows a peak value.

3. A method according to claim 1 wherein said analysis is carried out by plotting the time delay as an ordinate and the distance as an abscissa so as to predict the location of wear of the refractor walls.

4. A method according to claim 3 wherein said analysis further comprises interposing a phantom line between said plot of the time delay verses the distance and the abscissa.

5. A method according to claim 1 wherein said time delays at the different points are evaluated digitally from the following equation:

$$\phi_{ST_1}(n) = \frac{1}{M-n} \sum_{i=1}^{M-n} S(i)T_1(i+n)$$

$$(n = 0 \sim M)$$

wherein S represents the trigger signals, T is the temperature sensed by the temperature probe, $T_1$ is the temperature sensed at a specific one of the points, i, n is the lapse time, $\Delta\tau$ is the time delay and $\phi$ is the coefficient of the correlation between S and $T_1$.

6. A temperature probe assembly comprising:
    a sheath type enclosure;
    a first plurality of sheath type thermocouples or sheath type resistance thermometers comprising a first material juxtaposed within said sheath enclosure so as to locate respective temperature sensing areas at different points across the length of the probe assembly;
    a second plurality of sheath type thermocouples or sheath type resistance thermometers connected to the tips of the respective temperature sensing areas and comprising the first material; and
    an insulating filler disposed in said sheath enclosure with the first thermocouples or thermometers so as to be kept out of contact with each other within the sheath enclosure.

7. A temperature probe assembly comprising:
    a sheath enclosure;
    a first plurality of sheath type thermocouples or sheath type resistance thermometers comprising a first material juxtaposed within said sheath enclosure so as to locate respective temperature sensing areas at different points across the length of the probe assembly;
    a second plurality of sheath type thermocouples or sheath type resistance thermometers connected to the tips of respective temperature sensing areas so that the foremost ends of the respective sensing areas are flush with each other, the second thermocouples or thermometers comprising the first material; and
    an insulating filler inserted in said sheath enclosure with the first thermocouples or thermometers so as to be kept out of contact with each other within the sheath enclosure.

8. A temperature probe assembly according to claim 6 wherein said temperature probe is embedded in refractory walls of a blast furnace for monitoring the wear of the refractory walls.

* * * * *

UNITED STATES PATENT AND TRADEMARK OFFICE
CERTIFICATE OF CORRECTION

PATENT NO. : 4,358,953
DATED      : November 16, 1982
INVENTOR(S) : TAKEFUMI HORIUCHI ET AL It is certified that error appears in the above-identified patent and that said Letters Patent is hereby corrected as shown below:

In column 2, line 54, delete "analizing" and insert therefor --analyzing--;

In column 4, line 36, delete "as" before "ordinate" and insert therefor --the--;

In column 4, line 36, delete "as" before "abscissa" and insert therefor --the--;

In column 4, line 46, delete "by" after "crossed";

In column 5, line 2, delete "theroetically" and insert therefor --theoretically--;

In column 8, line 7, delete "verses" and insert -- versus --,

Signed and Sealed this

Seventh Day of June 1983

[SEAL]

Attest:

DONALD J. QUIGG

Attesting Officer　　Acting Commissioner of Patents and Trademarks